United States Patent
Kakileti

(10) Patent No.: US 10,198,670 B2
(45) Date of Patent: Feb. 5, 2019

(54) BLOOD VESSEL EXTRACTION IN TWO-DIMENSIONAL THERMOGRAPHY

(71) Applicant: Niramai Health Analytix Pvt. Ltd., Bangalore (IN)

(72) Inventor: Siva Teja Kakileti, Kakinada (IN)

(*) Notice: Subject to any disclaimer, the term of this patent is extended or adjusted under 35 U.S.C. 154(b) by 0 days.

(21) Appl. No.: 15/636,754

(22) Filed: Jun. 29, 2017

(65) Prior Publication Data

US 2018/0005085 A1  Jan. 4, 2018

Related U.S. Application Data

(60) Provisional application No. 62/356,238, filed on Jun. 29, 2016.

(51) Int. Cl.
| | |
|---|---|
| A61B 5/00 | (2006.01) |
| A61B 5/01 | (2006.01) |
| G06K 9/00 | (2006.01) |
| G06K 9/46 | (2006.01) |
| G06K 9/62 | (2006.01) |

(Continued)

(52) U.S. Cl.
CPC .......... *G06K 9/6267* (2013.01); *A61B 5/0075* (2013.01); *A61B 5/0077* (2013.01); *A61B 5/0091* (2013.01); *A61B 5/015* (2013.01); *A61B 5/489* (2013.01); *A61B 5/7264* (2013.01); *A61B 5/7282* (2013.01); *G06K 9/00885* (2013.01); *G06K 9/4647* (2013.01); *G06K 9/6202* (2013.01); *G06K 9/6214* (2013.01); *G06K 9/6269* (2013.01); *G06K 9/6271* (2013.01); *G06T 7/0012* (2013.01); *G06T 7/11* (2017.01); *A61B 2576/02* (2013.01); *G06K 2009/00932* (2013.01); *G06T 2207/10048* (2013.01); *G06T 2207/20021* (2013.01); *G06T 2207/20084* (2013.01); *G06T 2207/30068* (2013.01); *G06T 2207/30096* (2013.01); *G06T 2207/30101* (2013.01)

(58) Field of Classification Search
None
See application file for complete search history.

(56) References Cited

U.S. PATENT DOCUMENTS

2003/0171691 A1* 9/2003 Casscells, III ....... A61B 5/0075
600/549

* cited by examiner

*Primary Examiner* — Idowu O Osifade
(74) *Attorney, Agent, or Firm* — The Law Office of Austin Bonderer, PC; Austin Bonderer

(57) ABSTRACT

What is disclosed is a system and method for isolating blood vessels in a thermographic image of a patient's breast or any other muscular region of the body. A thermographic image of a patient is received. A temperature-based analysis is performed on the image to detect vessel pixels. An intensity-based method analysis is performed on the image. A shape-based analysis is also performed to detect pixels of vessel-like structures. Candidate pixels which satisfy one or more of intensity-based or temperature-based or shaped-based criterion are identified. A constraint of local maximallity is thereafter imposed on each candidate pixel that satisfies both criterion to eliminate spurious non-vessel pixels. Candidate pixels which satisfy both criterion are then marked with a different color such that the vessel structures in the breast tissue can be visually differentiated. The vessel structures are provided to a classifier system which classifies the tissue in the thermal image as malignant and non-malignant otherwise, based on a tortuosity of the vessel structures.

16 Claims, 5 Drawing Sheets

(51) Int. Cl.
*G06T 7/00* (2017.01)
*G06T 7/11* (2017.01)

BLOOD VESSEL EXTRACTION IN TWO-DIMENSIONAL THERMOGRAPHY

TECHNICAL FIELD

The present invention is directed to systems and methods for isolating blood vessels in a thermographic image of a person.

BACKGROUND

Breast cancer leads in incidence rates among all cancers in women, contributing to about one-fourth of the cancers detected. Such high incidence rates in the overall population, with nearly 1 in 8 women in the west and 1 in 11 women in India getting breast cancer sometime in their lifetime, requires intervention in terms of detection and treatment. Early detection is key to survival here as the breast cancer can be completely cured if detected in the early stages. Thermography is an emerging alternative non-radiation and non-contact screening method for breast cancer detection, whose sensitivity does not depend on the age of the woman. In the recent decade interest has been rekindled in thermography as a breast cancer screening approach with the improvement in thermal camera resolution and technology. Thermography can also be used for imaging other body parts and it accurately depicts the temperature distribution on the skin.

Malignancy increases the number of blood vessels. The experimental evidence for this dependence of malignant tumor growth and angiogenesis is known. Microcirculation is altered in cancer due to presence of nitric oxide which is released from cancerous tissue. This nitric oxide increases blood circulation creates new vessels and also recruits dormant vessels. By contact temperature measurements, it was observed that the malignant tumor is at a higher temperature than surrounding tissue. It was also observed that the malignant tumor is hotter than the temperature of blood vessels associated with the tumor. The increase in metabolic activity of the cancerous cells generates heat. This heat can be detected by a thermal camera. Malignancy also triggers regional changes to vessel shape and increases the vessel dimensions in terms of width and length compared to the normal vessels. The significant difference between the widths of normal and malignant blood vessels is due to increased blood supply. It is shown that tortuosity (twists and turns of vessel growth) is exhibited in early stages of cancer and that tumor vessels have a profound sort of tortuosity, with many smaller bends upon each larger bend. This increase in vessel caliber, vessel length, and its resultant tortuosity is also an effect of the increase in blood flow to the cancerous cells. It is important to be able to accurately isolate (extract) vessel structures in a thermographic image of breast tissue so that the tortuosity can be analyzed. The present invention is specifically directed to this effort.

BRIEF SUMMARY

The present invention is focused on breast cancer screening, and hence in extracting features from thermal images that will distinguish one or more malignant subsets from one or more subsets of the nonmalignant category. Some of these features will be having an association to the visual observations made by trained thermographers, but will not be exactly the same. The algorithm(s) to extract such features will be different in representation to the visual features and provide the advantage of quantifying the observations from thermal images. Other features are that difficult to interpret visually are additionally present, and have been designed due to their medical relevance to differentiate the malignant cases from some or more of the non-malignant cases. These features are divided into vascular and non-vascular features, and are described herein. The present invention extracts the blood vessels in thermal images even in presence of hotspots and non-uniform heat in images by considering intensity and shape based descriptors. One embodiment of the present method is used for isolating blood vessels in a thermographic image of a patient's breast involves the following. A thermographic image of a breast of a patient is received. A temperature-based analysis is performed on the image to detect vessel pixels. A shape-based analysis is also performed to detect pixels of vessel-like structures. Candidate pixels which satisfy both the temperature-based and shaped-based criterion are identified. A constraint of local maximality is thereafter imposed on each candidate pixel that satisfies both criterion to eliminate spurious non-vessel pixels. Candidate pixels which satisfy both criterion are then marked with a different color such that the vessel structures in the breast tissue can be visually differentiated. The vessel structures are provided to a classifier system which classifies the tissue in the thermal image as malignant and non-malignant otherwise, based on a tortuosity of the vessel structures.

Features and advantages of the above-described method will become readily apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which.

DETAILED DESCRIPTION

What is disclosed is a system and method for isolating blood vessels in a thermographic image of a patient.

Non-Limiting Definitions

A "patient" refers to either a male or a female person. Gender pronouns are not to be viewed as limiting the scope of the appended claims strictly to females. Moreover, although the terms "subject", "person" or "patient" are used interchangeably throughout this disclosure, it should be appreciated that the patient undergoing cancer screening may be something other than a human such as, for example, a primate. Therefore, the use of such terms is not to be viewed as limiting the scope of the appended claims to humans.

Figure 1:
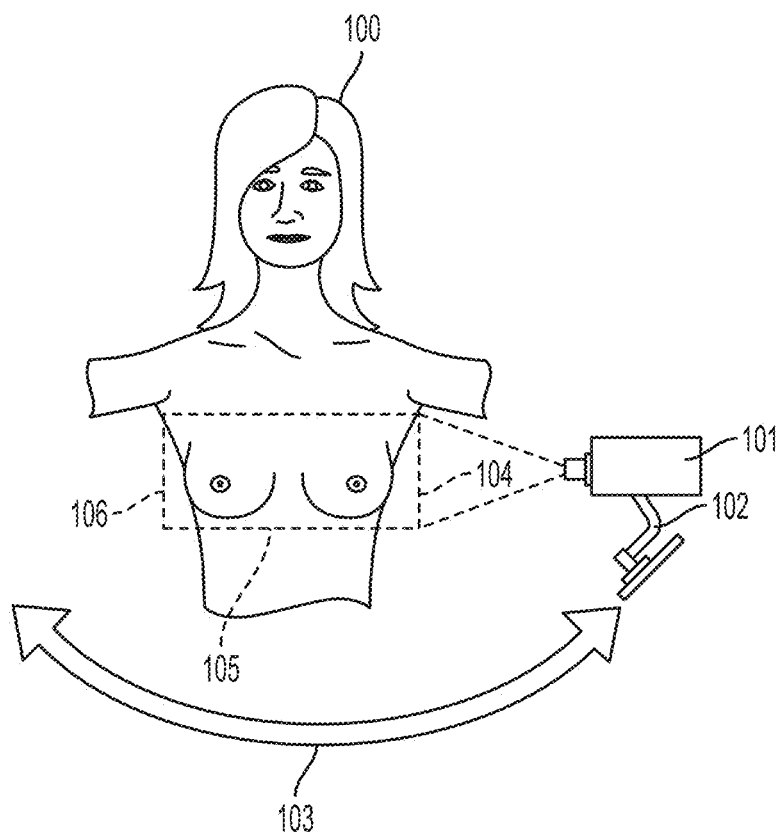
FIG. 1 shows an example female patient with a thermal camera mounted on a slideable and axially rotatable robotic arm for moving the camera along a semi-circular trajectory from side-to-side in front of the patient.

A "thermal camera" refers to either a still camera or a video camera with a lens that focuses infrared energy from objects in a scene onto an array of specialized sensors which convert infrared energy into electrical signals on a per-pixel basis and outputs a thermal image comprising an array of pixels with color values corresponding to temperatures of the objects in the image across a desired thermal wavelength band. FIG. 1 shows a thermal camera 101 mounted on a slideable and axially rotatable robotic arm 102 capable of moving the camera along a semi-circular trajectory 103 in the front of the patient from side-to-side such that thermographic images can be captured in a right-side view 104, a front view 105, and a left-side view 106, and various oblique angles in between. The thermal camera can be any of: a single-band infrared camera, a multi-band infrared camera in the thermal range, and a hyper spectral infrared camera in the thermal range. The resolution for a thermal camera is effectively the size of the pixel. Smaller pixels mean that more pixels will go into the thermal image giving the resulting image higher resolution and thus better spatial definition. Although thermal cameras offer a relatively large dynamic range of temperature settings, it is preferable that the camera's temperature range be relatively small, centered around the person's body surface temperature so that small temperature variations are amplified in terms of pixel color changes to provide a better measure of temperature variation. Thermal cameras are readily available in various streams of commerce. In one embodiment, the thermal camera is placed in wired or wireless communication with a workstation which enables manual or automatic control of various aspects of the thermal camera such as, for instance, adjusting a focus of the thermal camera lens, changing a resolution of the thermal camera, and changing a zoom level of the thermal camera.

A "thermographic image" or simply "thermal image" comprises a plurality of pixels with each pixel having an associated corresponding temperature value. Pixels in the thermal image with a higher temperature value being displayed in a first color and pixels with a lower temperature value are displayed in a second color. Pixels with temperature values between the lower and higher temperature values are displayed in gradations of color between the first and second colors. Thermal images can be retrieved from a memory or storage device of the thermal imaging device, or obtained from a remote device over a network. Thermal images may be retrieved from a media such as a CDROM or DVD. Thermal images may be downloaded from a web-based system which makes such images available for processing. Thermal images can also be retrieved using an application such as those which are widely available for handheld cellular devices and processed on the user's cellphone or other handheld computing device such as an iPad or tablet. Use of the term "image" is intended to also mean "video". This thermal image can also be stored and retrieved purely as a two-dimensional matrix of real numbered values (also known as radiometric image) which are derived as a function of the measured temperature values that are represented by the color of each pixel in the thermal image.

"Receiving a thermal image" of a patient for cancer screening is intended to be widely construed and includes retrieving, capturing, acquiring, or otherwise obtaining video image frames. The image can be received or retrieved from a remote device over a network, or from a media such as a CDROM or DVD. The image may be downloaded from a web-based system or application which makes video available for processing in accordance with the methods disclosed herein. The image can also be received from an application such as those which are available for handheld cellular devices and processed on the cellphone or other handheld computing device such as an iPad or Tablet-PC. The image can be received directly from a memory or storage device of the imaging device used to capture that image or video. The thermal image of the contralateral breast is analyzed to determine whether a hot spot exists in that breast.

A "classifier system" or simply "classifier" comprises at least a processor and a memory with the processor retrieving machine readable program instructions from memory and executing those instructions causing the processor to classify tissue in a thermal image of the breast based on the determined vesselness measure. In another embodiment, the tissue in the thermal image of the breast is classified based on the tortuosity of the vessel structures identified therein. Classifiers can take any of a variety of forms including a Support Vector Machine (SVM), a neural network, a Bayesian network, a Logistic Regression, Naïve Bayes, Randomized Forests, Decision Trees and Boosted Decision Trees, K-nearest neighbor, and a Restricted Boltzmann Machine (RBM), as are understood in the machine learning arts, including a hybrid system comprising any combination hereof. For an in-depth discussion, the reader is directed to any of a wide variety of texts on classifiers, including: "*Foundations of Machine Learning*", MIT Press (2012), ISBN-13: 978-0262018258, and "*Design and Analysis of Learning Classifier Systems: A Probabilistic Approach*", Springer (2008), ISBN-13: 978-3540798651. The classifier is training using a training set which, in various embodiments, comprises patient medical records and historical data. Based on the training set, the classifier sets a threshold value. Once trained, the classifier then utilizes the threshold for classification. The threshold can be user adjusted or user manipulated as needed to minimize false positives and/or false negatives. As new data sets or additional parameters are added to the training set used to train the classifier, the threshold or decision boundary used by the classifier will likely change accordingly.

It should be appreciated that the steps of "receiving", "analyzing", "communicating", "performing", "determining", "selecting", "providing", "identifying", "removing", and the like, as used herein, include the application of any of a variety of techniques as well as mathematical operations according to any specific context or for any specific purpose. Such steps may be facilitated or otherwise effectuated by a microprocessor executing machine readable program instructions such that the intended functionality is effectively performed.

Flow Diagram of One Embodiment

Figure 4:
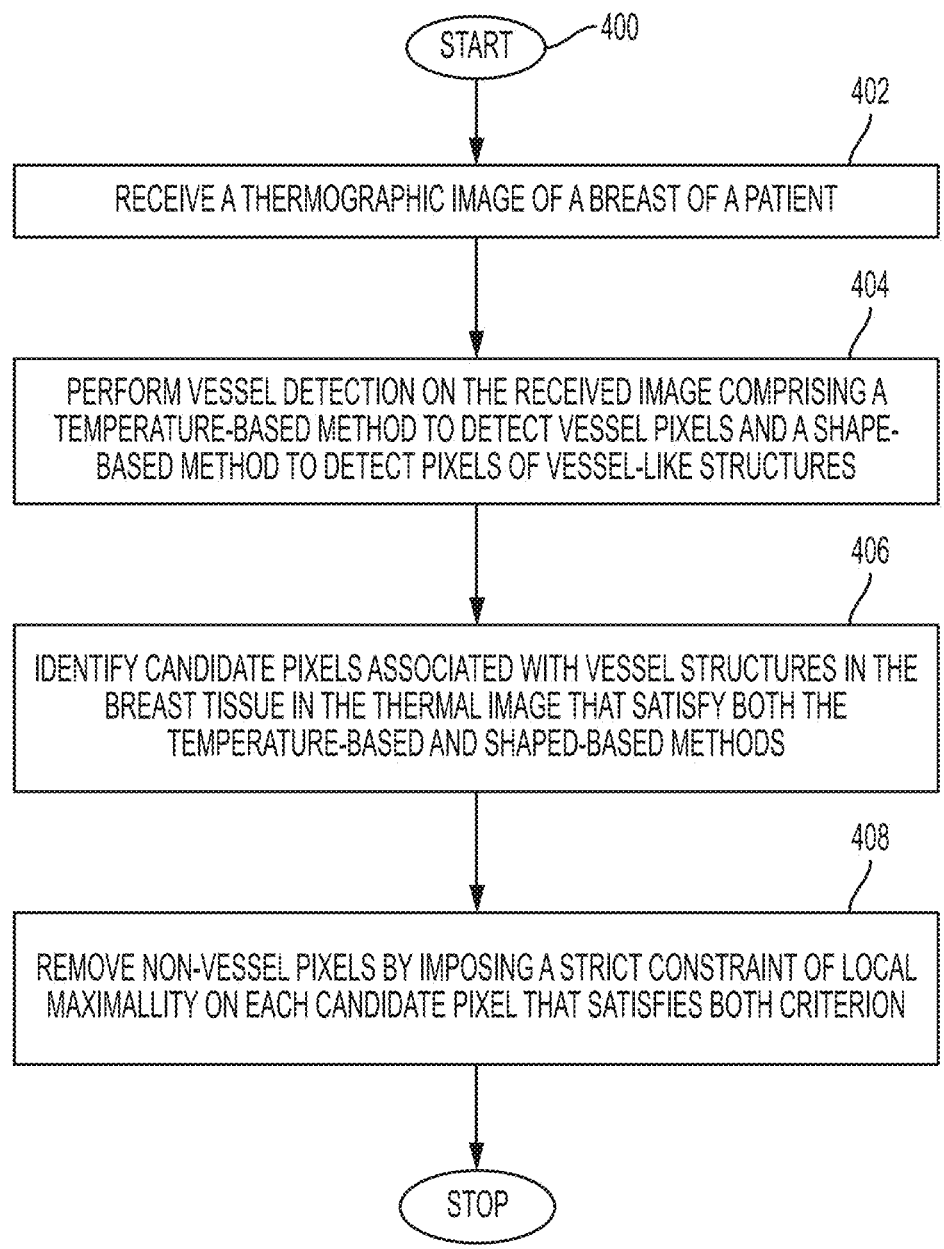
FIG. 4 is a flow diagram which illustrates one embodiment of the present method for isolating blood vessels in a thermographic image of a patient's breast.

Reference is now being made to the flow diagram of FIG. 4 which illustrates one embodiment of the present method for isolating blood vessels in a thermographic image of a patient's breast. Flow processing begins at step 400 and immediately proceeds to step 402.

Figure 2:
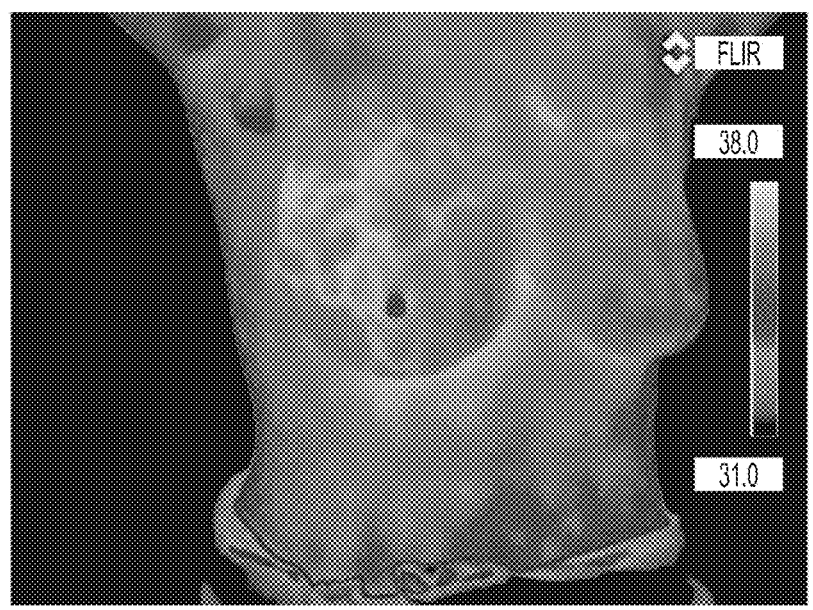
FIG. 2 shows a thermographic image of a breast of a patient.

At step 402, receive a thermographic image of a breast of a patient. The thermographic image can be a single image of both breasts or an image of either a left or right breast. FIG. 2 shows a thermographic image of a breast of a patient which is received for processing.

At step 404, perform vessel detection on the received image comprising a temperature-based method to detect vessel pixels and a shape-based method to detect pixels of vessel-like structures.

At step 406, identify candidate pixels associated with vessel structures in the breast tissue in the thermal image that satisfy both the temperature-based and shaped-based methods.

Figure 3:
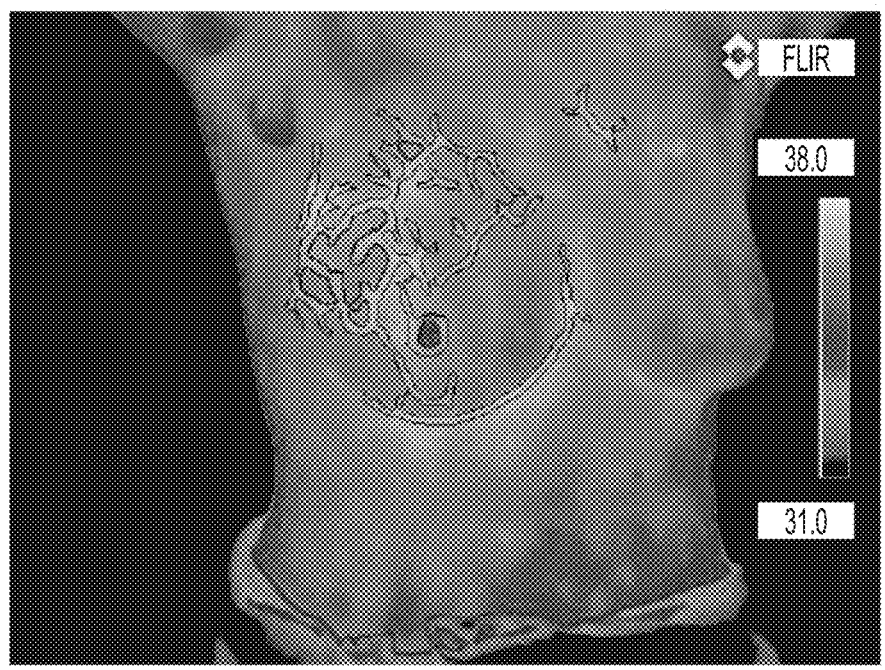
FIG. 3 shows the image of FIG. 2 which has been processed in accordance with the teachings hereof wherein the blood vessels have been identified.

At step 408, remove non-vessel pixels (from the pool of candidate pixels) by imposing a strict constraint of local maximallity on each candidate pixel that satisfies both criterion. FIG. 3 shows the image of FIG. 2 which has been processed in accordance with the teachings hereof wherein the blood vessels have been identified. In this embodiment further processing stops. In another embodiment, the remaining candidate pixels that satisfy both criterion are marked with a different color so that these pixels can be visually differentiated in the thermal image of the breast tissue. Thereafter, in this embodiment, the marked vessel structures are provided to a classifier system which classifies tissue in the breast as being malignant, and non-malignant otherwise, based on a tortuosity of the marked vessel structures.

It should be understood that the flow diagrams depicted herein are illustrative. One or more of the operations illustrated in the flow diagrams may be performed in a differing order. Other operations may be added, modified, enhanced, or consolidated. Variations thereof are intended to fall within the scope of the appended claims. All or portions of the flow diagrams may be implemented partially or fully in hardware in conjunction with machine readable/executable program instructions.

5.1 Automatic Extraction of Non-vascular Thermal Features

We want to differentiate the temperature increases due to malignancy from the rest of the non-malignancy conditions, as we are interested in cancer screening. For this, we first want to extract the region of increased temperature automatically.

Each feature is designed to differentiate malignancy from one or more of the non-malignancy cases. The temperature increase for malignancy is typically higher than for other non-malignancy cases. Hence, two different settings of this automatic extraction of the high temperature region is used, one tuned for malignancy and another tuned for non-malignancy cases. To distinguish malignancy from hormonal response, we design a feature to detect if there a similar increased temperature region in the contralateral breast in the corresponding region, as hormonal responses is expected to be present in both breasts. Malignancy in one breast causes the temperature rise in that breast to be significantly higher. To differentiate between benign conditions and malignancy, we use a feature to check if the boundary of the increased temperature region is regular or irregular. The boundaries of the malignant tumors are generally irregular, while the benign tumors are more regular. These features may be composed of multiple criteria, which are described in detail as follows.

These features are agnostic to the imaging protocols and the camera resolution. We have used 3 different types of cameras, each of different resolutions and dynamic range. We have used two imaging protocols: one with a video with the person rotating from one side to the other side so that all relevant views are observed, and another where 3 different angles, frontal/oblique/lateral views of each breast are taken. Features can be extracted from the video using the best view where the highest temperature region is most clearly seen (based on its area) in one breast, and the contralateral view of the other breast.

From the images, the best view corresponds to one of the 3 views in which the high temperature region is most prominently present.

Whether a tumor (likely malignant) is present: Tumor is defined to be a patch in the region satisfying the following conditions:
(1) The temperature of the region is above a threshold, given by the mean of the mode of the temperature histogram and the highest temperature present.
(2) The temperature of the region must be greater than or equal to (overall maximum temperature−2).
(3) The temperature of the region is less than or equal to the overall maximum temperature.
(4) The size of the region is greater than B pixels depending on camera resolution (say 64 pixels).

Number of hot patches (likely benign) in best view and its contralateral view: Hot patch (likely benign) is defined to be a patch in the region satisfying the following conditions:
(1) The temperature of the region is above a threshold, given by the mean of the medians of the temperatures in 3 views (frontal, lateral and oblique).
(2) The temperature of the region must be greater than or equal to (overall maximum temperature−2).
(3) The size of the region is greater than 64 pixels.

The size of the tumor/hot patch detected with respect to the Region of Interest in the best view.
(1) The size of the tumor or the hot patch divided by the size of corresponding Region of Interest.
(2) The size of the hot patch is considered in its contralateral view also, as it serves as a measure of symmetry for hormonal cases.

(D) Similarity of hot patch(es) in contralateral breast to distinguish hormonal response from malignancy.
(1) The extent of overlap of the tumor/hot patch present on one view and the corresponding contralateral view (if present):
  (i) Convolve the larger of the two increased temperature regions present in both breasts to determine the area of overlap and the percentage of overlap.
  (ii) In case of hot patches, lower temperature patches are also considered on the contra lateral side, to get a measure of the symmetry. These lower temperature hot patches are considered to be the hot patches with a lower threshold: (overall maximum temperature−3).
(2) The difference in area of the tumor/hot patch (if present, else it is 0) in the frontal/oblique/lateral views.

(E) The difference in temperature of the region of the tumor/hot patch detected and the surrounding region.
(1) This is calculated by taking the mean temperature of the ROI without the tumor/hot patch region detected in the best view, and the mean temperature of the tumor/hot patch region and their difference in considered.
(2) The difference of temperature is considered in the contralateral view also in case of hot patch as it accounts to the symmetry measure.

Irregularity of the tumor/hot patch shape with respect to a circle or ellipse.
(1) Irregularity measure with respect to a circle is calculated using the formula below.

$$Il(R) = \frac{1 + \sqrt{\pi} \max_{i \in R} \sqrt{(x_i - \bar{x})^2 + (y_i - \bar{y})^2}}{\sqrt{N(R)}} - 1$$

where $(x_i, y_i)$ are the points on the boundary, and $\bar{x}$ and $\bar{y}$ are the mean of $x_i$ and $y_i$, respectively, and $N(R)$ is the number of points within the region R.

(i) Irregularity measure is taken in the best view of the hot patch detected and also in its contralateral view.
(ii) In case of tumor, this measure is considered only in the best view.

(2) Deviation of the tumor shape from a best fitted ellipse. This is calculated by considering how much it deviates from the best fitted ellipse, by taking the dot product of the coefficient vector and the point coordinates. An ellipse can be defined as the set of points X=(x,y) such that F(a,X)= f(a, (x,y))=D·a=0, where D=($x^2$, xy, $y^2$, x, y,1) and a=($a_{xx}$, $a_{xy}$, $a_{yy}$, $a_x$, $a_y$, $a_1$) and $4a_{xx}a_{yy} - a_{xy}^2 > 0$ for an ellipse. This is equivalent to $a^T$ Ca>0, where C is a 6×6 matrix with values, $C_{1,3}=C_{3,1}=2$, $C_{2,2}=-1$, and all other $C_{i,j}=0$. We can fit the ellipse to N data points, by minimizing the distance $\Delta(a,x) = \Sigma f(a, x_i)^2 = \Sigma(a^T D_i^T D_i a) = a^T Sa$, where $S=\Sigma(D_i^T D_i)$. So, find a such that $\Delta(a,x)$ is minimum and $a^T Ca = \theta$ for some positive θ. To solve the above constrained problem, introduce a LaGrange multiplier λ and a LaGrangian $L(a) = \Delta(a,x) - \lambda(a^T Ca - \theta)$ and minimize L(a), $$\frac{dL(a)}{da} = 0, \; Sa = \lambda Ca, \; \frac{1}{\lambda}a = S^{-1}Ca.$$

Solving the above eigen value problem with Eigen value 1/λ, we get the Eigen vector a, which gives us the equation of the ellipse. The measure by which the tumor boundary deviates from this ellipse is given by the dot product of D and a.

(3) Deviation of the tumor shape from a circle with center as centroid of all the points. This is calculated by taking the standard deviation of the distances of the points of the tumor boundary from the centroid of the tumor. The distances are calculated as $d_i=(x_i-\bar{x})^2+(y_i-\bar{y})^2$, where $\bar{x}$ and $\bar{y}$ are the centroid of $x_i$ and $y_i$. The standard deviation of these distances is calculated as: Std deviation σ=sqrt $((\Sigma(d_i-\bar{d})^2)/n)$, where $\bar{d}$ is the mean of the distances $d_i$ and n is the number of points in the boundary.

5.2 Automatic Extraction of Vascular Features

Vascular Features play an important role in the classification of malignancy. The importance of these features can also be seen from their significant role in classification with other modalities like MRI, Mammogram while classification/grading. In fact, thermographers consider these features during thermo-biological grading. In thermography, normal blood vessels are detected only when they show significant temperature difference than surrounding tissues. In case of malignancy, heat radiated from the vessels increases due to large amount of blood flow, which can be captured in the radiometric image/thermo-gram. To design and analyze the features from blood vessels, we first need to extract the blood vessels from the Region of Interest (ROI). Section 5.2.1 gives details of the blood vessel extraction in thermography. After extraction, the vascular features are mentioned in Section 5.2.2.

5.2.1 Automatic Extraction of Blood Vessels

Existing 2D vessel detection algorithms, when applied on thermo-graphic images, fail in extracting the vessels properly. Instead they might even pick up diffusions of heat and edges of tumor as vessels. The present algorithm extracts the blood vessels correctly even in presence of hotspots and non-uniform heat in images by considering intensity and shape based descriptors. The present algorithm uses matched filter response of a vertically shifted Gaussian as an enhancement technique followed by a vesselness criterion defined by us to extract the vessel like structures based on their shape from the Eigen values of Hessian Matrix. We use morphological extraction of vessels to detect the pixels based on their intensity relative to the surroundings. The pixels that are detected in both cases are considered as vessel pixels. This kind of approach might pick edges of tumor/hotspot as vessel pixels in some cases of thermo-graphic images due to irregular diffusion of heat in breast region. To avoid that, we used right and left Gaussians for calculating matched filter response separately to extract the valid blood vessel pixels which would be discussed in the algorithm.

Matched Filter:

Vessels are darker than the background and can be approximated to an inverted Gaussian curve along x-axis shifted by its absolute mean with vessel direction along y-axis. This kind of matched filter response approach for detecting blood vessels is proposed in references [1] *"Detection Of Blood Vessels In Retinal Images Using Two-Dimensional Matched Filters"*, Chaudhuri, S.; Chatterjee, S.; Katz, N.; Nelson, M.; Goldbaum, M., IEEE Transactions on Medical Imaging, Vol. 8, No. 3, pp. 263-269 (1989), [2] *"An Efficient Algorithm For Extraction Of Anatomical Structures In Retinal Images"*, Thitiporn, C. and Fan, G. L., Proc. Of Intl. Conf. on Image Processing, vol. 1, pp. 1093-1096 (2003), and [3] *"Retinal Vessel Extraction By Matched Filter With First-Order Derivative Of Gaussian"*, Zhang B, et al., Computers In Biology And Medicine, 40:438-445, (2010). This matched filter can be mathematically written as:

$$f(x, y) = \left\{ A\left(1 - \exp\left(-\frac{x^2}{\sigma^2}\right)\right) - E\left(A\left(1 - \exp\left(-\frac{x^2}{\sigma^2}\right)\right)\right) \right\} \quad (1)$$

$$|y| \leq \frac{H}{2}, \text{otherwise}$$

where A represents the amplitude, σ corresponds to half the width of the vessel, and E(.) represents expected/mean value. It is sufficient to assume σ as the half of maximum width of the vessel in f(x,y). The response for each pixel is calculated by rotating f(x,y) from 0° to 180° in the steps of 15° and convolving with the image to find the peak response at every pixel. This peak is obtained when vessel aligns in the direction of f(x,y) centered at that pixel. In references [1-3], vessel pixels are determined by binarizing the matched filter response with a proper threshold. These strict thresholds might not work properly and do not give satisfactory results in some cases. Instead of binarizing, we use this threshold to stretch the image to get an enhanced image. This can be done by replacing every pixel greater than threshold with the value of threshold followed by stretching within the limits [0,255]. This final enhanced image can be used to classify into vessel or not.

We use a thresholding mechanism proposed in reference [3] as an enhancement technique. This is calculated as the gray level value which maximizes the sum of entropies of gray level transition with in object and gray level transition between the object & background. This can be mathematically analyzed as follows: Let $T=[t_{ij}]$ represents the Gray Level Co-occurrence Matrix (GLCM) which is defined as:

$$t_{ij} = \sum_{p=1}^{m} \sum_{q=1}^{n} \begin{cases} 1 & \text{if} \begin{cases} I(p, q) = i \text{ and } I(p, q+1) = j \\ \text{or} \\ I(p, q) = i \text{ and } I(p+1, q) = j \end{cases} \\ 0 & \text{otherwise} \end{cases}$$

Probability of GLCM, probability that two pixels are adjacent, is obtained as:

$$P_{ij} = \frac{t_{ij}}{\sum_i \sum_j t_{ij}}$$

Let $H_A(T_h)$ and $H_C(T_h)$ represent the entropies of gray level transition with in object and gray level transition between the object & background at threshold $T_h$. If L represents number of number of gray levels in the image then from the entropy definition $$H_A(T_h) = -\frac{1}{2} \sum_{i=1}^{T_h} \sum_{j=1}^{T_h} P_{ij}^A \log(P_{ij}^A)$$

where:

$$P_{ij}^A = \frac{P_{ij}}{\sum_{i=1}^{T_h} \sum_{j=1}^{T_h} P_{ij}}$$

and $$H_C(T_h) = -\frac{1}{2} \sum_{i=T_h+1}^{L} \sum_{j=T_h+1}^{L} P_{ij}^C \log(P_{ij}^C)$$

where:

$$P_{ij}^C = \frac{P_{ij}}{\sum_{i=T_h+1}^{L} \sum_{j=T_h+1}^{L} P_{ij}}$$

The final threshold can be calculated as:

$$T = \underset{0 \leq T_h \leq L}{\mathrm{argmax}} H_A(T_h) + H_C(T_h) \quad (2)$$

Threshold T is used to enhance the image.

Multi Scale Shape Based Vessel-ness Criterion:

In order to classify whether a pixel in an image is part of a vessel or not, we can analyze the Eigen values of the Hessian matrix H. These Eigen values give lot of information about the pixels curvature. The Eigen vectors of H represent the curvature of the vessel at that pixel. In case of dark vessels with bright background (tube like structures), the smallest Eigen value points in the direction of the vessel with $|\lambda_2| \approx 0$ and $|\lambda_1| \gg |\lambda_2|$. This is previously observed and vesselness function for classification of a pixel has been proposed by reference [4] *"Multi-Scale Vessel Enhancement Filtering"*, A. Frangi, W. Niessen, K. Vincken, M. Viergever, Medical Image Computing and Computer-Assisted Intervention MICCAI 98, pp. 130-137, (1998).

We define a new vesselness function as follows:

$$V_s(\lambda_1, \lambda_2) = \begin{cases} \mathrm{sign}\left(\mathrm{sinc}\left(\frac{|\lambda_2|}{|\lambda_1| - |\lambda_2|}\right) - t\right) & \lambda_1 < 0 \\ 0 & \text{otherwise} \end{cases} \quad (3)$$

Here, $V_s$ represents vessel-ness at scale sand converges to 0 for tube like structures, to 1 for blob/sheet like structures. The value of t denotes the threshold value for deciding whether the pixel is a vessel or not. It is observed that, a pixel detected as a vessel in lower scales will also be detected as a vessel in upper scales to some extent due to the diffusion of heat from blood vessels. Based on this, the final criterion for vesselness is defined as:

$$V = \underset{s_{min} \leq s \leq s_{max}}{\mathrm{mode}} V_s(\lambda_1, \lambda_2)$$

Taking mode instead of maximum helps in eliminating some of the noise and spurious pixels which might be detected as a vessel at a particular scale. Also, using maximum for calculating overall response can lead to misclassification of pixels that are close to the vessel. Using mode can prevent it and helps in getting the predicted width of vessel equals to actual width. Values of $s_{min}$, $s_{max}$ are carefully chosen so that the pixel belonging to vessel are not eliminated. We can use any function for $V_s$ with a proper threshold. Some examples are:

$$V_s^s(\lambda_1, \lambda_2) = \begin{cases} \mathrm{sign}\left(\mathrm{sinc}\left(\frac{\lambda_2}{\lambda_1 - \lambda_2}\right) - t_s\right) & \lambda_1 > 0 \\ 0 & \text{otherwise} \end{cases} \quad (4)$$

Morphological Vessel Segmentation

Image is divided into non overlapping blocks of size [A1 A2]. Each of these blocks are then converted to binary by setting their respective block mean as threshold. As intensity of vessel pixels are locally minimum, this thresholding sets these pixels to 1 if they are less than mean of the block and to 0 otherwise. An intersection of different window sizes starting from maximum window size [A1max, A2max] to minimum window size [A1min, A2 min] are taken with a step ratio 'r' to get proper thin boundaries of vessels. The maximum value of window size can be taken as image size and the minimum window size is set corresponding to vessel width. This morphological vessel detection as an intensity based approach to detect the blood vessels in breast region. The final accuracy of vessel extraction can be improved with better morphological vessel enhancement techniques.

Algorithm for Blood Vessel Extraction:
1) Convert the given RGB image into LAB color space where L represents lightness and a and b represent color opponents.
2) Ostu's segmentation, as described in reference [6] *"A Threshold Selection Method From Gray-Level Histogram"*, Nobuyuki Otsu, IEEE Transactions on Sys. Man. And Cybernetics, Vol. 9, No. 1, pp. 62-66 (January 1979) is used on L to segment out the human body from the background region.
3) The obtained image consists of bright vessels with dark back ground. Complement the image to make the vessels darker.
4) Vessel pixels have peak response when Matched Filter (MF) response is calculated using vertically-shifted Gaussian as well as from using left and right vertically-shifted Gaussian's. This is because the vessel profile at the center of pixel is the combination of these left and right Gaussian Kernels. Enhanced images from MF response corresponding to left Gaussian ($f^l$), right Gaussian ($f^r$) and Full Gaussian Kernels ($f^g$) are calculated using:

$$f^l(x, y) = \left\{ A\left(1 - \exp\left(-\frac{x^2}{\sigma^2}\right)\right) - E\left(A\left(1 - \exp\left(-\frac{x^2}{\sigma^2}\right)\right)\right) \right\}$$

$$f^r(x, y) = \left\{ A\left(1 - \exp\left(-\frac{x^2}{\sigma^2}\right)\right) - E\left(A\left(1 - \exp\left(-\frac{x^2}{\sigma^2}\right)\right)\right) \right\}$$

$$-\frac{H}{2} \le y \le 0, \text{otherwise}$$

$$0 \le y \le \frac{H}{2}, \text{otherwise}$$

$$f^g(x, y) = \left\{ A\left(1 - \exp\left(-\frac{x^2}{\sigma^2}\right)\right) - E\left(A\left(1 - \exp\left(-\frac{x^2}{\sigma^2}\right)\right)\right) \right\}$$

$$|y| \le \frac{H}{2}, \text{otherwise}$$

5) Stretch these MF responses obtained in step 4 with the respective thresholds obtained from Eq. (2).
6) To each of these enhanced images, apply morphological vessel segmentation to get the locally minimum pixels. Denote these corresponding responses as $p^l$, $p^r$, $p^g$.
7) Vessel-ness measure is calculated for each of the enhanced images obtained in step 5 with thresholds t,t,0 respectively. 't' can be set to 0.5 for vesselness measure ($V_s$) in Eq.(3). Let the outputs be $V^l$, $V^r$, $V^g$, respectively.
8) Take the corresponding intersections of morphological segmentation and vesselness measure to get the pixels that satisfies both shape and intensity based conditions.

$$F^A = P^A \cap V^A$$

where A={l,r,g}.
9) Classify a pixel as a vessel pixel only if it is detected in both Left and Right enhanced images.

$$F^l = F^r \cap F^l$$

10) These detected vessels in $F^l$ are disconnected. Re-connecting these vessel pixels to get continuous vessels is done using $F^g$. $F^g$ might pick up some of the spurious vessels also. So we remove those vessels which are not at all present in $F^l$. $F^l$ is the final output that detects the blood vessels. We may still get some spurious cases which can be eliminated by Spurious Vessel Removing.

Spurious Vessel Removing

Spurious vessels elimination is done by removing the vessels that are not detected as a vessel when you traverse along the gradient direction with window size greater than width of vessel (W). This is implemented as follows
  (1) For each detected vessel, select those pixels whose difference between their intensity and mean intensity of pixels in the window [3*W, L] along the gradient direction is less than zero. This gets us the tube like structures that can be segmented from background. L is a small value and takes value in 1, 2, 3, . . . W/4.
  (2) Central line of the vessel has minimum intensity along the normal at every point on the line. With the help of this, we select those pixels which are locally minimum along their gradient direction as well as in the opposite direction in a window [1, W]. The center line for blob like structures cannot be detected as they don't satisfy this criterion. Dilation followed by intersection with the image gets us the actual vessels by removing the blob like pixels.
  (3) For each detected vessel, calculate the probability of it being a vessel.

$$P(\text{vessel}) = \frac{\text{total number of pixels detected in both } i \& ii}{\text{total number of pixels in the detected vessel}}$$

where P represents the probability that a component is vessel. For blob like structures, P is low due to low pixel count obtained from steps 1 and 2.
  (4) Starting with maximum length vessel, remove those vessels whose P is less than 0.3 or length is less than 30 pixels with no nearby detected vessel components.

5.2.2 Vascular Features

As mentioned, vascular features play an important role in classification of malignancy. To extract the features from vessels, they are skeletonized using some of standard algorithms like distance transform. Short false vessel branches obtained using these algorithms are eliminated by putting a threshold on the length of vessel branch. Reiterating on the medical basis given in Section 3, the length, calibre, tortuosity, of the vessels increase in malignancy, and additional vessels and increased vessel density are due to angiogenesis. The temperature of these vessels associated/generated by malignancy is also higher. Features to extract these are mentioned below. In the contralateral normal breast, there will be a difference in the vascularity from the malignant breast. There will be similar vascularity present in both sides of normal subjects. Based on this, a vascular symmetry feature is designed to differentiate between normal and malignant subjects. In addition to these medically relevant vascular features, we also want to see if some additional features can be empirically validated. These are described next.

Number of Blood Vessels:

As the presence of malignant tumor triggers the neo-angiogenesis, these features play an important role while classification of malignancy. The vessel ends are obtained based on the branch point with more than 2 connected components (in the skeletal vessel) or the end point based on 1 connected component. Each vessel is removed after finding its ends and the blood vessel count is increased. This is repeated till no more vessels remain.

Mean Temperature:

As mentioned, blood vessels in malignancy provide more blood supply, thus generating more heat. Mean temperature for each blood vessel is calculated as:

$$T^i_{mean} = \frac{1}{n} \sum_n T^i(n)$$

where $T_{mean}{}^i$ represents the mean temperature of pixels in the $i^{th}$ blood vessel.

Tortuosity:

Tortuosity tells us how twisted/tortuous the blood vessels are. Existing methods are described in references [7] *"Measuring Tortuosity Of The Intracerebral Vasculature From MRA Images"*, Bullitt, E., Gerig, G., Pizer, S. M., Lin, W., Aylward, S. R., IEEE Transactions on Medical Imaging, 22(9), pp. 1163-1171 (2003), [8] *"Automated Measurement of Retinal Vascular Tortuosity"*, Hart, W. E. et al., Proc. AMIA Annual Fall Symposium, pp. 459-463. (Fall, 1997), and [9] *"Image Processing Techniques For The Quantification Of Atherosclerotic Changes"*, K. Chandrinos, M. Pilu, R. Fisher, and P. Trahanias, Dai Research Paper, (1998). We will explore further also and choose a tortuosity method which will give better classification results with our data set.

Mean Calibre:

Calibre is the diameter of vessel. During malignancy, the vessels are dilated (calibre increases) to supply blood to the tumor region. Hence, this feature plays an important role in classification normal and malignant. Calibre is defined for each modified skeleton point as twice the shortest distance between skeleton pixel and boundary of blood vessel. Mean of this gives the average vessel diameter for that vessel.

Density:

Density is defined as the ratio of vessel area to the region of interest (ROI). This gives us an estimate of how a vascular is the breast region. As stated, malignancy increases vascularity which in turn supply large amount of blood to tumor region and thus increasing temperature. Since this is clearly visible in radiometric images, density plays a crucial role in classification.

Symmetry:

This feature plays a significant role in classifying malignancy especially in distinguishing with normal cases. We want to see the symmetry in vascular patterns between both breasts. For this, we use shape descriptors for vessels and vessel location to specify the vascular pattern. If the vascular pattern descriptors are similar in both breasts, then it would likely correspond to normal cases.

Validation of Features:

We see whether these features play an important role in classification of breast cancer through empirical validation.

i) Mean number of branches: We test how this plays an important role while classification and also validate whether number of branches increases during malignancy. This is calculated by counting the vessel segments for each vessel tree after removing branch points.
 ii) Extent of blood vessels: The area covered by the blood vessels with respect to the ROI is computed provide the extent. The min and max of the x and y coordinates of vascularity gives an approximate idea of the area covered.
 iii) Location: For each vessel, a centroid is calculated. The location of vessel is defined with respect to the centroid of ROI using the distance and angle between them.

5.3 Medical History Features

The thermal patterns change with age and the presence of non-malignant conditions. There are also several breast cancer risk factors which can help in breast cancer screening. Some of these can be easily obtained from a questionnaire on medical history and self/clinical examination. These would help in improving the sensitivity/specificity in cancer screening when used along with thermography. These are listed below.

a) Age of the person/patient.
 b) The presence of lumps in right and left breast observed in clinical history.
 c) Presence of lumps in previous clinical examinations
 d) Approximate Hormone levels present on the day of thermographic examination, estimated using date of last
 e) Menstrual period, and time period of menstrual cycle
 f) Personal history of breast cancer or other cancer
 g) Presence of BRCA1/BRCA2 genes
 h) Family history of breast cancer or ovarian cancer
 i) Other relevant medical conditions, such as pregnant/lactating, recent breast surgery, inflammation, infectious conditions, etc.

5.4 Automatic Classification of Extracted Features

The basic two classes in which the subjects can be classified are malignant and non-malignant. Thermal increase can be seen in malignant, benign as well as hormonal response cases in addition to other non-malignant conditions. Further, within malignant cases, there may be differences in thermal patterns for different conditions. We use one classifier for each non-malignant and malignant category, which has a distinct thermal pattern to other sub-classes. However, we are not interested in errors within non-malignant sub-classes or errors within malignant sub-classes, as our goal is cancer screening. Hence, we train with multiple categories and test with only two classes (malignant/nonmalignant). We have used standard classifiers like Support Vector Machine (SVM) and Random Forests (RF) in our implementation described in Section 6. We found that Random Forests provide better sensitivity/specificity. This is because the features designed are well suited to decision trees and the random forest classifier uses a set of decision trees to improve upon accuracy.

Block Diagram of Image Processing System

Figure 5:
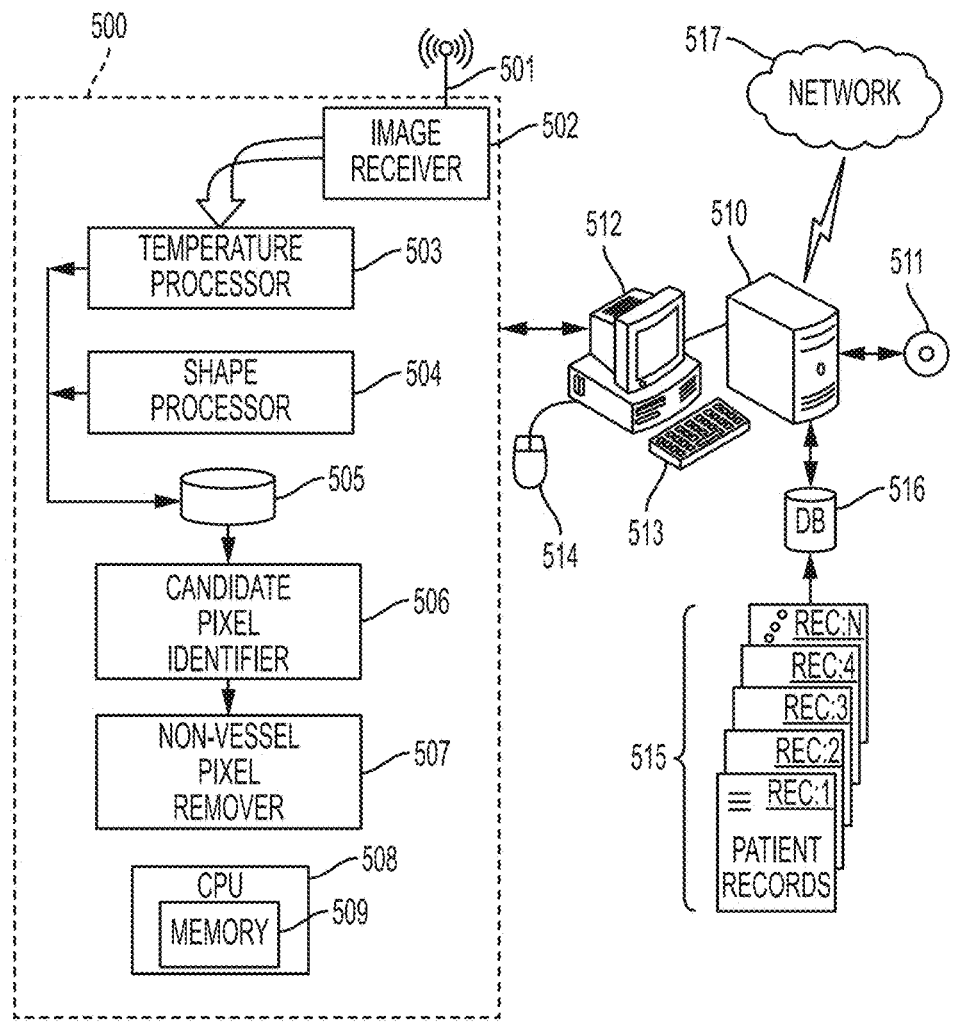
FIG. 5 which shows a functional block diagram of one example image processing system for processing thermographic images for breast cancer screening in accordance with the embodiment described with respect to the flow diagram of FIG. 4.

Reference is now being made to FIG. 5 which shows a functional block diagram of one example image processing system 500 for processing thermographic images for breast cancer screening in accordance with the embodiment described with respect to the flow diagram of FIG. 4.

Image Receiver 502 wirelessly receives the video via antenna 501 having been transmitted thereto from the video imaging device 101 of FIG. 1. Temperate Processor 503 performs a temperature-based method to detect vessel pixels in the received image. Shape Processor 504 performs a shape-based method to detect pixels of vessel-like structures in the received image. Both Modules 503 and 504 store their results to storage device 505. Candidate Pixel Identifier Module 506 retrieves the results of the temperature-based and shape-based methods from storage device 505 and proceeds to identify candidate pixels associated with vessel structures in the breast tissue in the thermal image that satisfy both the temperature-based and shaped-based methods. Non-Vessel Pixel Remover Module 507 receives the candidate pixels from Module 506 and proceeds to remove non-vessel pixels by imposing a strict constraint of local maximallity on each candidate pixel that satisfies both criterion. Central Processing Unit 508 retrieves machine readable program instructions from a memory 509 and is provided to facilitate the functionality of any of the modules of the system 500. CPU 508, operating alone or in conjunction with other processors, may be configured to assist or otherwise perform the functionality of any of the modules or processing units of the system 500 as well as facilitating communication between the system 500 and the workstation 510.

System 500 is shown having been placed in communication with a workstation 510. A computer case of the workstation houses various components such as a motherboard with a processor and memory, a network card, a video card, a hard drive capable of reading/writing to machine readable media 511 such as a floppy disk, optical disk, CD-ROM, DVD, magnetic tape, and the like, and other software and hardware needed to perform the functionality of a computer workstation. The workstation further includes a display device 512, such as a CRT, LCD, or touch screen device, for displaying information, images, classifications, computed values, extracted vessels, patient medical information, results, interim values, and the like. A user can view any of that information and make a selection from menu options displayed thereon. Keyboard 513 and mouse 514 effectuate a user input. It should be appreciated that the workstation has an operating system and other specialized software configured to display alphanumeric values, menus, scroll bars, dials, slideable bars, pull-down options, selectable buttons, and the like, for entering, selecting, modifying, and accepting information needed for processing in accordance with the teachings hereof. The workstation is further enabled to display thermal images, hot spots, vessel structures and classifications as they are derived. A user or technician may use the user interface of the workstation to set parameters, view/adjust/delete pixel values, and adjust various aspects of the temperature-based and/or the shape-based methods being performed, as needed or as desired, depending on the implementation. Any of these selections or inputs may be stored/retrieved to storage device 511. Default settings can be retrieved from the storage device. A user of the workstation is also able to view or manipulate any of the data in the patient records, collectively at 515, stored in database 516. Any of the received images, results, extracted vessels, and the like, may be stored to a storage device internal to the workstation 510. Although shown as a desktop computer, the workstation can be a laptop, mainframe, or a special purpose computer such as an ASIC, circuit, or the like. The embodiment of the workstation of FIG. 6 is illustrative and may include other functionality known in the arts.

Any of the components of the workstation may be placed in communication with any of the modules and processing units of system 500. Any of the modules of the system 500 can be placed in communication with storage devices 505, 516 and 106 and/or computer readable media 511 and may store/retrieve there from data, variables, records, parameters, functions, and/or machine readable/executable program instructions, as needed to perform their intended functions. Each of the modules of the system 500 may be placed in communication with one or more remote devices over network 517. It should be appreciated that some or all of the functionality performed by any of the modules or processing units of the system 500 can be performed, in whole or in part, by the workstation. The embodiment shown is illustrative and should not be viewed as limiting the scope of the appended claims strictly to that configuration. Various modules may designate one or more components which may, in turn, comprise software and/or hardware designed to perform the intended function.

The teachings hereof can be implemented in hardware or software using any known or later developed systems, structures, devices, and/or software by those skilled in the applicable art without undue experimentation from the functional description provided herein with a general knowledge of the relevant arts. One or more aspects of the methods described herein are intended to be incorporated in an article of manufacture which may be shipped, sold, leased, or otherwise provided separately either alone or as part of a product suite or a service. It will be appreciated that the above-disclosed and other features and functions, or alternatives thereof, may be desirably combined into other different systems or applications. Presently unforeseen or unanticipated alternatives, modifications, variations, or improvements may become apparent and/or subsequently made by those skilled in this art which are also intended to be encompassed by the following claims. The teachings of any publications referenced herein are hereby incorporated by reference in their entirety.

What is claimed is:

1. A method for determining a region of blood vessels in a thermographic image of a subject, the method comprising:
   receiving, from a thermographic camera, a thermographic image of a subject, wherein the thermographic image is captured by a thermographic imaging camera, the thermographic imaging camera comprising:
      an array of sensors that converts infrared energy into electrical signals on a per-pixel basis;
      a lens that focuses the infrared energy from the subject's upper body onto the array of sensors, wherein the array of sensors detects temperature values from the subject's upper body; and
   a specialized processor that processes the detected temperature values into at least one block of pixels to generate the thermographic image;
   determining candidate pixels associated with vessel-like structures in the thermographic image that satisfies at least one of the temperature-based method or the shaped-based method;
   transforming the thermographic image into a transformed thermographic image by eliminating non-vessel pixels from the determined candidate pixels by implementing a strict constraint of local maximality on each candidate pixel;
   identifying pixels associated with the vessel structures in the transformed thermographic image; and
   generating a segmented thermographic image using the identified pixels associated with the vessel structure and displaying boundaries of the identified blood vessels in the thermographic image of the subject with a separate color.

2. The method of claim 1, wherein the temperature-based method comprises:
   transforming the thermographic image into non-overlapping blocks of pixels of a predefined size; and
   binarizing each of said non-overlapping blocks with a threshold that is equal to a mean of pixels in that block.

3. The method of claim 1, wherein the shape-based method comprises:

$$V_s(\lambda_1, \lambda_2) = \begin{cases} \text{sign}\left(\text{sinc}\left(\frac{|\lambda_2|}{|\lambda_1| - |\lambda_2|}\right) - t\right) & \lambda_1 < 0 \\ 0 & \text{otherwise} \end{cases}$$

where $V_s$ is the vessel-ness measure at scale s, t is a threshold for deciding vessel and non-vessel areas, $\lambda_1$, $\lambda_2$, are Eigenvectors of a Hessian matrix, where $|\lambda_1| \geq |\lambda_2|$, and $V_s=1$ for tubular structures, and $V_s=0$ or $V_s=-1$, otherwise.

4. The method of claim 1, further comprising of a classifier system that is provided with marked vessel structures in the thermographic image of a tissue of the subject, wherein the marked vessel structures are provided to the classifier system to detect abnormal vascular patterns in different parts of the body of the subject based on the marked vessel structures.

5. The method of claim 1, further comprising of the classifier system that is provided with the marked vessel structures in the thermographic image of a tissue of the subject, wherein classifier system classifies the subject tissue as malignant, and non-malignant, based on symmetry, tortuosity, number of vessels, length of vessels, caliber, branch length and other parameters of the vessel structures.

6. The method of claim 5, wherein the classifier system comprises any of:
   Support Vector Machine, a neural network, a Bayesian network, a Logistic regression, Naïve Bayes, Randomized Forests, Decision Trees and Boosted Decision Trees, K-nearest neighbor, a Restricted Boltzmann Machine, and a hybrid system comprising any combination hereof.

7. A method of claim 1, wherein the blood vessel structures are detected based on temperature of the pixels, intensity of pixels or a shape-based method to detect a patch of pixels that are vessel-like structures, wherein said shape-based method further comprises
   obtaining the pixels that have (a) a higher curvature along direction of the vessel-like structures and (b) a lower curvature along its perpendicular direction, as described by a vessel-ness measure at scale (Vs); and detecting the pixels that have both the higher curvature along direction of the vessel-like structures and the lower curvature along its perpendicular direction at multiple scales.

8. A system for determining a region of blood vessels in a thermographic image of a subject, the system comprising:

a storage device; and a processor retrieving machine-readable instructions from the storage device which, when executed by the processor, enable the processor to:

receive a thermographic image of the subject, wherein the thermographic image is captured by a thermographic imaging camera, the thermographic imaging camera comprising:

an array of sensors that converts infrared energy into electrical signals on a per-pixel basis;

a lens that focuses the infrared energy from an upper body of the subject onto the array of sensors, wherein the array of sensors detects temperature values from the upper body of the subject; and a specialized processor that processes the detected temperature values into at least one block of pixels to generate the thermographic image;

pixels of vessel-like structures determine candidate pixels associated with vessel-like structures in the thermographic image that satisfies at least one of the temperature-based method or the shaped-based methods;

transform the thermographic image into a transformed thermographic image by eliminating non-vessel pixels from the determined candidate pixels by implementing a strict constraint of local maximality on each candidate pixel;

identify pixels associated with said vessel structures in the transformed thermographic image;

communicate the candidate pixels that satisfy both criterion to the storage device; and generating a segmented thermographic image using the identified pixels associated with the vessel structures to displaying boundaries of the identified blood vessels in the thermographic image of the subject with a separate color.

9. The system of claim 8, wherein the temperature-based method comprises:

transforming the thermographic image into non-overlapping blocks of pixels of a predefined size; and binarizing each of said non-overlapping blocks with a threshold that is equal to a mean of pixels in that block.

10. The system of claim 8, wherein the shape-based method comprises:

$$V_s(\lambda_1, \lambda_2) = \begin{cases} \text{sign}\left(\text{sinc}\left(\frac{|\lambda_2|}{|\lambda_1| - |\lambda_2|}\right) - t\right) & \lambda_1 < 0 \\ 0 & \text{otherwise} \end{cases}$$

where $V_s$ is the vessel-ness measure at scale s, t is a threshold for deciding vessel and non-vessel areas, $\lambda_1$, $\lambda_2$ are Eigenvectors of a Hessian matrix, where $|\lambda_1| \geq |\lambda_2|$, and $V_s=1$ for tubular structures, and $V_s=0$ or $V_s=-1$, otherwise.

11. The system of claim 8, further comprising marking vessel pixels which satisfy both criterion in the image with a different color such that the vessel structures in the thermal image of the subject tissue can be visually differentiated.

12. The system of claim 11, further comprising communicating the marked image to any of: a display device, the storage device, and a remote device over a network.

13. The system of claim 11, further comprising of the classifier system that is provided with the marked vessel structures in the thermographic image of a tissue of the subject, wherein classifier system classifies the subject tissue as malignant, and non-malignant, based on symmetry, tortuosity, number of vessels, length of vessels, caliber, branch length and other parameters of the vessel structures.

14. The system of claim 13, wherein the classifier system comprises any of:

Support Vector Machine, a neural network, a Bayesian network, a Logistic regression, Naïve Bayes, Randomized Forests, Decision Trees and Boosted Decision Trees, K-nearest neighbor, a Restricted Boltzmann Machine, and a hybrid system comprising any combination hereof.

15. The system of claim 13, further comprising communicating the classification to any of: a display device, the storage device, and a remote device over a network.

16. The system of claim 8, wherein the blood vessel structures are detected based on temperature of the pixels, intensity of pixels or a shape-based method to detect a patch of pixels that are vessel-like structures, wherein said processor further enabled to obtain the pixels that have (a) a higher curvature along direction of the vessel-like structures and (b) a lower curvature along its perpendicular direction, as described by a vessel-ness measure at scale (Vs); and detect the pixels that have both the higher curvature along direction of the vessel-like structures and the lower curvature along its perpendicular direction at multiple scales.

* * * * *